United States Patent [19]

Malley et al.

[11] Patent Number: 5,736,526
[45] Date of Patent: Apr. 7, 1998

[54] MIXTURES OF DDI AND D4T WITH HYDROXYCARBAMIDE FOR INHIBITING RETROVIRAL REPLICATION

[75] Inventors: Serge D. Malley, Villeurbanne; Jorge R. Vila, Lyons, both of France

[73] Assignee: Compagnie de Development Aguettant S.A., France

[21] Appl. No.: 577,322

[22] Filed: Dec. 22, 1995

Related U.S. Application Data

[60] Division of Ser. No. 401,488, Mar. 8, 1995, which is a continuation-in-part of Ser. No. 378,219, Jan. 25, 1995, abandoned, which is a continuation-in-part of Ser. No. 169,253, Dec. 20, 1993, Pat. No. 5,521,161.

[51] Int. Cl.$^6$ .................. A61K 31/70; A61K 31/17
[52] U.S. Cl. .................. 514/45; 514/50; 514/588; 536/27.14; 536/27.8; 536/28.2; 536/28.54; 564/301
[58] Field of Search .................. 514/45, 46, 49, 514/50, 588; 536/27.14, 28.2, 27.8, 28.54; 564/301

[56] References Cited

U.S. PATENT DOCUMENTS

| | | | |
|---|---|---|---|
| 4,708,818 | 11/1987 | Montagnier et al. | 435/5 |
| 5,026,687 | 6/1991 | Yarchoan et al. | 514/45 |
| 5,110,600 | 5/1992 | Green | 424/45 D |
| 5,300,059 | 4/1994 | Rubinstein et al. | 604/408 |

FOREIGN PATENT DOCUMENTS

| | | |
|---|---|---|
| 0206497 | 12/1986 | European Pat. Off. . |
| 9427590 | 12/1984 | WIPO . |
| 8701284 | 3/1987 | WIPO . |

OTHER PUBLICATIONS

Meyerhans et al, "The Intracellular Nucleotide Pool Effects HIV Replication", VIII International Conference on AIDS/ III STD World Congress, vol. 2, Jul. 1992, pp. A22–ABSM No. 2118.
T'Ang et al, "Optimization of the Schiff Bases of N–Hydroxy–N'aminoguanidine as Anticancer and Antiviral Agents", J. Med. Chem., vol. 28(8) 1985, pp. 1103–1106.
Lien, "Ribonucleotide reductase inhibitors as anticancer and antiviral agents", Progress in Drug Research, vol. 31, 1987, pp. 101–126.
Lori et al, "Hydroxyurea Inhibits HIV–1 Replication by Inducing Low dNTP Levels. A Cellular Enzyme as a Target to Inhibit HIV–1", Antiviral Res., vol. 23/Sup. 1, 1994, p. 53.
Gao et al, "Anti–HIV–1 Activity of Hydroxyurea in Combination with 2', 3'–dideoxynucleosides", Clinical Research, vol. 42, No. 2, 1994, p. 280A.
Matsumoto et al, "Inhibition of RNA Synthesis by Deoxyadenosine Plus Deoxycoformycin in Resting Lymphocytes", The Journal of Immunology, vol. 131(6), 1983, pp. 2762–2766, Dec.

International Search Report for Internation Application No. PCT/US 94/05515, Dec. 8, 1994, Publication WO 94/27590, PTO–892 ref. N.
Balzarini et al, "2',3'–Dideoxycytidine: Regulation of its Metabolism and Anti–retroviral Potency by Natural Pyrimidine Nucleosides and by Inhibitors of Pyrimidine Nucleotide Synthesis", Molecular Pharmacology, vol. 32, 1987, pp. 798–806.
Safrin et al, "Potential for Combined Therapy with 348U87, a Ribonucleotide Reductase Inhibitor, and Acyclovir as Treatment for Acyclovir–Resistant Herpes Simpley Virus Infection", Journal of Medical Virology Supplement 1, 1993, pp. 146–149.
Wilson et al, "Purinogenic Immundeficiency Disease —Differential Effects of Deoxyadenosine and Deoxy–guanosine on DNA Synthesis in Human T Lymphoblasts", J. Clin. Invest., vol. 64, 1979, pp. 1475–1484, Nov.
Albert et al, "Deoxyadenosine Toxicity and Cell Cycle Arrest in Hydroxyurea–Resistant S49 T–Lymphoma Cells", Experimental Cell Research, vol. 179, 1988, pp. 417–428.
Perno et al, "Inhibition of Human Immunodeficiency Virus (HIV–1/HTLV–III$_{Ba-L}$) Replication in Fresh and Cultured Human Peripheral Blood Monocytes/Macrophages by Azidothymidine and Related 2',3'–Dideoxynucleosides", J. of Exp. Medicine, vol. 168, pp. 1111–1125, Sep..
Fischl, "Treatment of HIV Disease in 1993/1994", AIDS Clin. Rev., vol. 94, 1993, pp. 167–187.
Gao et al., "Low Levels of Deoxynucleotides in Peripheral Blood Lymphocytes: A Strategy to Inhibit Human Immunodeficiency Virus Type 1 Replication," Proc. Nat. Acad. Sci. USA, 90, 8925–8928(1990).
Biochemicals/Organic Compounds for Research and Diagnostic Reagents, Sigma Chemical Co. (catalog), St. Louis, MO, 1992, pp. 321,341–342.
Feorino et al., "Prevention of Activation of HIV–1 by Antiviral Agents in OM–10.1 Cells," Antiviral Chemistry & Chemotherapy, 4(1), 55–63 (1993).
U.S. application No. 08/65,814, Lori et al., filed May 21, 1993.
Snyder et al.(I), "Effects of Hydroxyurea and Thymidine Derivatives on the Uptake and Metabolism of Deoxycytidine and Arabinosylcytosine in Log Phase and Contact–Inhibited Human Diploid Fibroblast," Mol. Pharmacol., 28(6), 574–580 (1985); see p. 578 in particular.
Licastro et al., "Inhibition of Polymerases–$\alpha$ and –$\beta$ Completely Blocks DNA Repair Induced by UV Irradiation in Cultured Mouse Neuronal Cells," Biochem. Biophys. Res. Comm., 132(3), 929–933 (1985).

(List continued on next page.)

Primary Examiner—John Kight
Assistant Examiner—L. Eric Crane

[57] ABSTRACT

A method and composition for inhibiting the spread of a retrovirus such as HIV in a human cell population in which a retrovirus such as HIV is present has been found. The spread of the retrovirus is inhibited by treatment of the cells with a synergistic combination mixture of a dideoxyribonucleoside excluding AZT and hydroxycarbamide.

16 Claims, 3 Drawing Sheets

OTHER PUBLICATIONS

Busso et al., "Cellular Pharmacology and Anti–HIV Activity of 2',3'-Dideoxyguanosine," *AIDS Res. Human Retroviruses*, 6(9), 1139–1146 (1990).

R. S. Root–Bernstein(I), "AIDS is More Than HIV: Part I," *Genetic Engineering News*, Sep. 1, 1992, pp. 4–6.

R. S. Root–Bernstein(II), "AIDS is More Than HIV: Part II," *Genetic Engineering News*, Sep. 15, 1992, pp. 4–5.

"Kaposi's Sarcoma and *Pneumocystis* Pneumonia Among Homosexual Men," *Morbidity Mortality Weekly Rept.*, vol. 30(25), Centers for Disease Control, Jul. 3, 1981, pp. 305–308.

Barre–Sinoussi et al., "Isolation of a T–Lymphotropic Retrovirus from a Patient at Risk for Acquired Immune Deficiency Syndrome (AIDS)," *Science*, 220, 868–871 (1983).

Fauci, "The Human Immunodeficiency Virus: Infectivity and Mechanisms of Pathogenesis," *Science*, 239, 617–622 (1988).

Fauci, "Multifactoral Nature of Human Immunodeficiency Viruses Disease: Implications for Therapy," *Science*, 262, 1011–1018 (1993).

Zack et al., "HIV–1 Entry into Quiescent Primary Lymphocytes: Molecular Analysis Reveals a Labile, Latent Viral Structure," *Cell*, 61, 213–222 (1990).

Bukrinsky et al., "Quiescent T Lymphocytes as an Inducible Virus Reservoir in HIV–1 Infection," *Science*, 254, 233–237 (1991).

Schnittman et al., "The Reservoir for HIV–1 in Human Peripheral Blood is a T Cell that Maintains Expression of CD4," *Science*, 245, 305–308 (1989).

Fox et al., "Lymphoid Germinal Centers Are Resevoirs of Human Immunodeficiency Virus Type 1 RNA," *J. Infectious Diseases*, 164, 1051–1057 (1991).

Hirsch et al., "Therapy for Human Immunodeficiency Virus Infection," *N. Engl. J. Medicine*, 328(23), 1686–1695 (1993).

Pauwels et al., "Rapid and Automated Tetrazolium–Based Colorimetric Assay for the Detection of Anti–HIV Compounds," *J. Virological Methods*, 20, 309–321 (1988).

Yarchoan et al., "Clinical Pharmacology of 2'Azido–2', 3'-dideoxythymidine (Zidovudine) and Related Dideoxynucleosides," *N. eng. J. medicine*, 321,(11), 726–738 (1989).

Chow et al., "Use of Evolutionary Limitations of HIV–1 Multidrug Resistance to Optimize Therapy," *Nature*, 361, 650–654 (1993).

Lori et al., "Hydroxyureas an Inhibitor of Human Immunodeficiency Virus–Type 1 Replication," *Science*, 266, 801–805 (1994).

Karlsson et al., "Hydroxyurea Increases the Phosphorylation of 3'-fluorothymidine and 3'–Azidothymidine in CEM Cells," *Eur. J. Biochem.*, 186, 689–694 (1989).

Marquez et al., "Acied–Stable 2'–Fluoro Purine Dideoxynucleosides as Active Agents Against HIV," *J. Med. Chem.*, 33(3), 978–985 (1990).

Snyder et al. (II), "The Accumulation of DNA Breaks Due to Incision; Comparative Studies with Various Inhibitors," Ch. 2 in *DNA Repai et al. r and Its Inhibition, Nucleic Acids Symposium Series No. 13*, Collins et al., eds., IRL Press, Oxford, England, 1984, pp. 13–33.

Biron et al., "Anti–HIV Activity of the Combination of Didanosine and Hydroxyurea in HIV–1 Infected Individuals," *J. AIDS and Human Retrovirology*, 10(1), 36–40 (Aug. 1995).

Balzarini et al., "The Anti–HTLV–III (Anti–HIV) and Cytotoxic activity of 2', 3'–Didehydro–2', 3'–dideoxyribonucleosides: A Comparison with Their Parental 2', 3'–dideoxyribonucleosides," *Mol. Pharmacol.*, 32, 162–167 (1987).

Malley et al.(I), "Suppression of HIV Production in Resting Lymphocytes by Combining Didanosine and Hydroxamate Compounds," *The Lancet*, 343(8908), 1292 (1994).

Hao et al., "Factors Determining the Activity of 2', 3'–Dideoxynucleosides in Suppressing Human Immunodeficiency Virus In Vitro," *Molecular Pharmacology*, 34, 431–435 (1988).

Medina et al., "Ganciclovir Antagonizes the Anti–Human––Immunodeficiency Virus Type I Activity of Zidovudine and Didanosine In Vitro," *Antimicrobial Agents and Chemotherapy*, 36(5), 1127–1130 (1992).

"Study Puts Risk of H.I.V. in Young U.S. Men at 1 in 92," *New York Times*, (National Ed.), Nov. 24, 1995, p. B19.

Simonelli et al., "Hydroxyurea as an Antiretroviral Drug in HIV Infected Patients: Clinical, Immunological and Virological Evaluation," Abstract No. 84, in Book of abstracts from *The Fifth European Conference on Clinical Aspects and Treatment of HIV Infection*, European AIDS Clinical Society (publ.), Copenhagen, Denmark, Sep. 26–29, 1995.

L. K. Altman, "Study Challenges AZT Role As the Chief Drug for H.I.V.," *New York Times*, (Sec. 1), Sunday, Sep. 17, 1995, p. 38.

Langreth, "FDA Gives Approval to Glaxo, Sequus To Market Separate AIDS Therapies," *The Wall Street Journal*, Nov. 21, 1995, p. B12.

Malley et al.(II), "Synergistic Anti–Human Immunodeficiency Virus Type 1 Effect of Hydroxamate Compounds with 2', 3'–Dideoxyinosine in Infected Resting Human Lymphocytes," *Proc. Nat. Acad. Sci. USA*, 91, 11017–11021 (Nov. 1994).

MIXTURES OF DDI AND D4T WITH HYDROXYCARBAMIDE FOR INHIBITING RETROVIRAL REPLICATION

This application is a divisional of U.S. Ser. No. 08/401, 488, filed Mar. 8, 1995, which is a continuation-in-part of U.S. Ser. No. 08/378,219, filed Jan. 25, 1995, now abandoned, which is a continuation-in-part of U.S. Ser. No. 08/169,253 filed Dec. 20, 1993, now U.S. Pat. No. 5,521,161 issued May 28, 1996, all hereby incorporated by reference.

FIELD OF THE INVENTION

The present invention relates to a combination of a reverse transcriptase inhibitor and hydroxycarbamide in a synergistically effective amount wherein the combination is useful in inhibiting retroviral spread.

BACKGROUND OF THE INVENTION

The expression "Acquired Immuno-Deficiency Syndrome" (AIDS) was first used in 1981 to describe a state of cellular immune deficiency in homosexuals, characterized by the appearance of opportunistic infections and Kaposi's Sarcoma evolving very aggressively (CDC (Center for Disease Control), MMWR, 30: 305–308.DC, (1981)). In 1983 a retrovirus since called HIV (Human Immunodeficiency Virus type 1) was isolated among AIDS patients (Barré-Sinoussi F. et al *Science*, 220: 868–870 (1983)).

Over the past several years, researchers and clinicians have gained considerable experience in studying and caring for individuals infected with HIV throughout the often prolonged course of HIV disease and AIDS. On the basis of this experience, it has become clear that the pathogenic mechanisms underlying HIV infection and disease are not unidimensional, but rather are extremely complex (Fauci A S., *Science*, 239, 617, (1988)). Any attempt to design a comprehensive therapeutic strategy for HIV disease must take this fact into account. (Fauci, 1993, *Science*, 262:1011–1018).

After entry of the HIV virus into cells and uncoating of the HIV particle, reverse transcription of the viral RNA genome into DNA replicas occurs. Among several forms of unintegrated viral DNA (now containing the long repeats [LTRs], at both the 5' and the 3' ends), only the two-LTR linear forms can integrate into the host genome. Such a process appears strictly dependent upon cell activation/replication of T lymphocytes, although "resting" T cells are clearly susceptible to HIV infection. (Zack J. A. et al, *Cell;* 61, 213–222, (1990)). Furthermore, part of the reverse transcription process also can occur in unactivated T cells, a process that results in the accumulation of incomplete DNA molecules, which may persist for several hours and remain capable of being integrated into the host genome if cell sufficient activation (Zack J. A. et al, *Cell;* 61, 213–222, (1990)). Therefore, infected "resting" CD4+T lymphocytes can be considered a transient viral reservoir in infected individuals (Bokrinsky M. I. et al; *Science*, 254, 423–427, (1991)). These observations are of particular importance in anatomic compartments such as the peripheral blood and lymphoid organs, where the CD4+T cell subset represents the predominant infected cell type (Schmittman S M. et al, *Science*, 245,305–308, (1989)); (Fox C H. et al *J. Infect Dis;* 164, 1051–1057, (1991)).

The above discussion provides a sound scientific basis for blocking the initial burst of virus replication and dissemination as well as the persistent replication throughout the course of disease by treating HIV-infected individuals with anti-retroviral agents from the earliest time that HIV infection is recognized through the entire course of infection. Unfortunately, currently available agents are only partially effective in suppressing virus replication and spread, and this effect is transient (Hirsch M S, et al, *New Engl. J. Med.* 328 1686, (1993)). Clear cut, but limited, benefit is seen when 3'-azido-2',3'-dideoxythymidine or azidothymidine (AZT) is given to a patient with advanced HIV disease, and the benefits of early intervention are usually only temporary and do not result in significant long-term advantages with regard to the course of disease and death. (Fauci, 1993, *Science*, 262:1011–1018).

A number of 2'-3'-dideoxynucleosides have been found to be useful for the treatment or prophylaxis of retroviral infections and especially HIV and AIDS. Examples of such materials include: 2',3'-dideoxy-cytosine (ddC); 2',3'-dideoxy-adenosine (ddA); 2',3'-dideoxy-guanosine (ddG); 2',3'-dideoxy-inosine (ddI) 2',3' dideoxy-thymidine (ddT); 2'deoxy-3' thiocytidine (3TC); and 2',3'-didehydro-3'-deoxythymidine (d4T). See European patent application 0206497 and published PCT application number WO 87/01284.

Hydroxycarbamide (HC) was initially synthesized over 120 years ago and has been found to demonstrate activity against a broad spectrum of tumors. (Donehower, Seminars in Oncology, Vol. 19, No. 3, Suppl. 9 (June) 1992: pp 11–19). Additionally, hydroxycarbamide has been used as a viricide. In published PCT application number WO 93/09718, hydroxycarbamide is taught to be useful in a hydrogel polymer coating of a blood bag in order to inhibit viral and infectivity.

Gao et al (*PNAS, USA*, Vol. 90, pp. 8925–8928, October 1993) disclose that hydroxyurea (hydroxycarbamide) treatment of peripheral blood lymphocytes (PBLs) decreases dNTP levels and the DNA synthesis rate to levels comparable to quiescent PBLs. The article alleges a possible use of hydroxyurea in AIDS therapy.

However, there still remains a need for more effective treatments for the suppression of retroviruses and, in particular, the prevention and/or inhibition of HIV and viral spread. By viral spread, it is intended to include the inhibition of viral replication, and also may include the ability of inhibiting the virus to infect a further host cells.

Objectives of the present invention in the search for new antiretroviral agents include:

1) the identification of compounds with less toxicity and antiviral activity greater than AZT.

2) the development of drug combinations which provide an additive or synergistic effect and decrease the probability of drug resistant isolates.

BRIEF SUMMARY OF THE INVENTION

The present invention relates to a combination of a reverse transcriptase inhibitor and hydroxycarbamide in a synergistic combination wherein the synergistic combination is capable of preventing and/or inhibiting the spread of retroviruses including HIV. More specifically, the present invention relates to a method of preventing and/or inhibiting the spread of retroviruses, including HIV (HIV-1 and HIV-2), HTLV-1, HTLV-2, SIV or HSV, by exposing a cell population, including cells infected by a retrovirus such as, for example, HIV, to a synergistic combination of a reverse transcriptase inhibitor and hydroxycarbamide. Additionally, the present invention encompasses the treatment of HIV-infected and AIDS patients with a synergistic combination of a reverse transcriptase inhibitor and hydroxycarbamide in order to prevent and/or inhibit the spread of HIV in these patients.

In a preferred embodiment of the present invention, the reverse transcriptase inhibitors include dideoxynucleosides, such as, for example, ddI, ddA, ddG, ddT (DT4), 3TC and d4T.

In particular and in the preferred combination of the present invention, it has been found that a synergistic combination of hydroxycarbamide (HC) and 2',3'-dideoxy-inosine (ddI) can be formed which is especially effective in preventing and/or inhibiting HIV spread. The preferred embodiment of the invention encompasses a composition including a pharmaceutical composition comprising a synergistic combination of ddI and HC. The pharmaceutical composition can optionally contain a pharmaceutically acceptable carrier and/or excipient and/or vehicle. The preferred method of the instant invention comprises preventing and/or inhibiting retroviral or HIV spread by treating a cell population, including cells infected with HIV, with a synergistic combination of ddI and HC. Additionally, the preferred method comprises treating an HIV infected or AIDS patient with a synergistic combination of ddI and HC so as to prevent and/or inhibit HIV spread in the patient.

DETAILED DESCRIPTION OF THE INVENTION

The following examples of specific embodiments of the present invention are offered for illustrative purposes only and are not limiting with respect to the scope of the disclosure or claim coverage.

Testing of the mixture of dideoxyinosine (ddI) and hydroxycarbamide (HC) on the spread of the HIV virus was conducted under three types of conditions:

a) CD4+ lymphocytes purified from PBMC, and infected with HIV virus without prior activation/proliferation of these cells by phytohemagglutinin (PHA) and interleukin-2 (IL-2).

b) PBMC preactivated by PHA and IL-2, then infected with the HIV virus.

c) in HIV-infected individuals

EXAMPLE 1

The activity of the mixture of ddI and HC on non-activated CD4+ lymphocytes, infected with HIV virus was studied.

Non-activated CD4+ cells were infected, then treated for 7 days by HC, ddI or the combination of the two, then activated by PHA and IL-2 (PHA-IL-2).

Cellular viability between 90% and 100% was observed during the first seven days after infection, both for the infected control and for the infected cells treated with the two drugs separately or in combination. Comparable proliferative cellular response was observed in the presence of PHA-IL-2 for the first 3 days (days 7–9) both in the six virus infected groups and in the non-infected, non-treated donor CD-4+ cells. This proliferative response is associated with cytopathic effect in the infected control group, and in the groups treated with HC alone at 0.05 and 0.15 mM: these groups had greater than 50% loss of viability compared to the uninfected control group; this effect is due to viral replication and is accompanied by large-scale production of p24-HIV in the culture supernatant seen at day 15 (86215 pg of p24/ml for the infected control, 75470 and 82005 for 0.05 and 0.15 mM HC treatment groups, respectively) see FIG. 1.

The cytopathic effect was observed later for the cells treated with 5 µM ddI and reached substantially the same level of p24 production as the infected control 10 days later at day 25 (101080 pg p24/ml), see FIG. 1.

Figure 1:
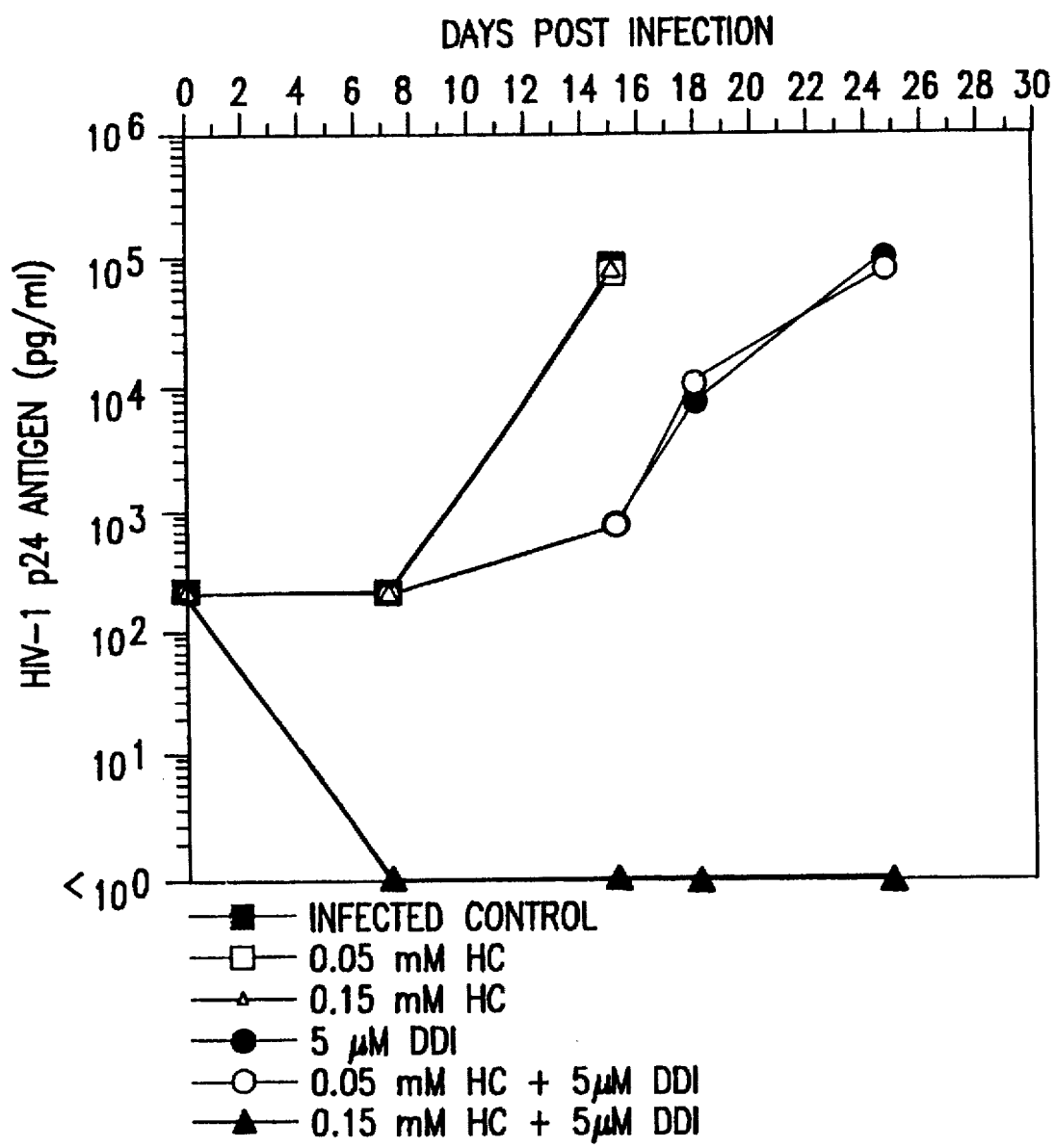
FIG. 1 is a study of the anti-viral activity of a mixture of ddI and HC on non-activated CD4+ lymphocytes infected with the HIV virus.

The mixture of HC at 0.05 mM with ddI at 5 µM does not substantially change the viral replication profile as compared to ddI alone (84883 pg p24/ml at day 25), see FIG. 1.

By contrast, a surprising synergistic effect is observed with the combination 0.15 mM of HC and 5 µM of ddI, where no residual viral production is detectable (<1 pg p24/ml) at day 7 and day 25 despite cellular proliferation which is identical to the non-treated, non-infected control (>90% cell viability measured by MTT test).

FIG. 1, in particular, shows a study of the activity of a mixture of ddI and HC on non-activated CD4+ lymphocytes infected with the HIV virus. The CD4+ lymphocytes were purified from PBMC with immunomagnetic beads (Dynabeads® M450). These cells were infected with the HIV-1 virus strain IIIB at a multiplicity of infection of 5 000 tissue culture infectious dose (TCID) per $10^6$ cells (241 pg/ml p24 antigen equivalent of virus). After 2 hours of virus-cell contact, the cells were washed twice and placed in the culture medium RPMI 1640 (supplemented with 10% fetal calf serum (FCS), 2 mM glutamine, penicillin 100 IU/ml and Streptomycin 100 µg/ml) at a density of $1.3 \times 10^6$ cells/ml. ddI was immediately added at a concentration of 5 µM and HC at concentrations of 0.05 mM and 0.15 mM. The drugs and culture medium were partially renewed (50%) on day 4, maintaining the same concentration of each. On day 7, in order to remove the drugs, the cells were washed twice and put back in culture in the presence of PHA at a concentration of 1 µg/ml and recombinant IL-2 at a concentration of 20 U/ml. This culture was maintained until day 25, with partial renewal (50%) of the medium twice a week. The number of viable cells was quantified by a tetrazolium-based colorimetric 3-(4,5-dimethylthiazol-2-yl)-2,5-diphenyltetrazolium bromide (MTT) method (Pauwels, R. et al *J. Virol. Methods,* 20, 309–321, (1988)), and activity is expressed as a percentage of the signal in the drug-free and virus-free control. Viral replication was quantified by measuring the HIV-1 p24 antigen by ELISA using the Dupont de Nemours kit.

EXAMPLE 2

In order to determine whether or not this synergistic effect of ddI in a mixture with HC is specific to ddI, or whether a similar effect could be observed with AZT, a parallel study was conducted combining HC with azidothymidine (AZT) with surprising results.

Figure 2:
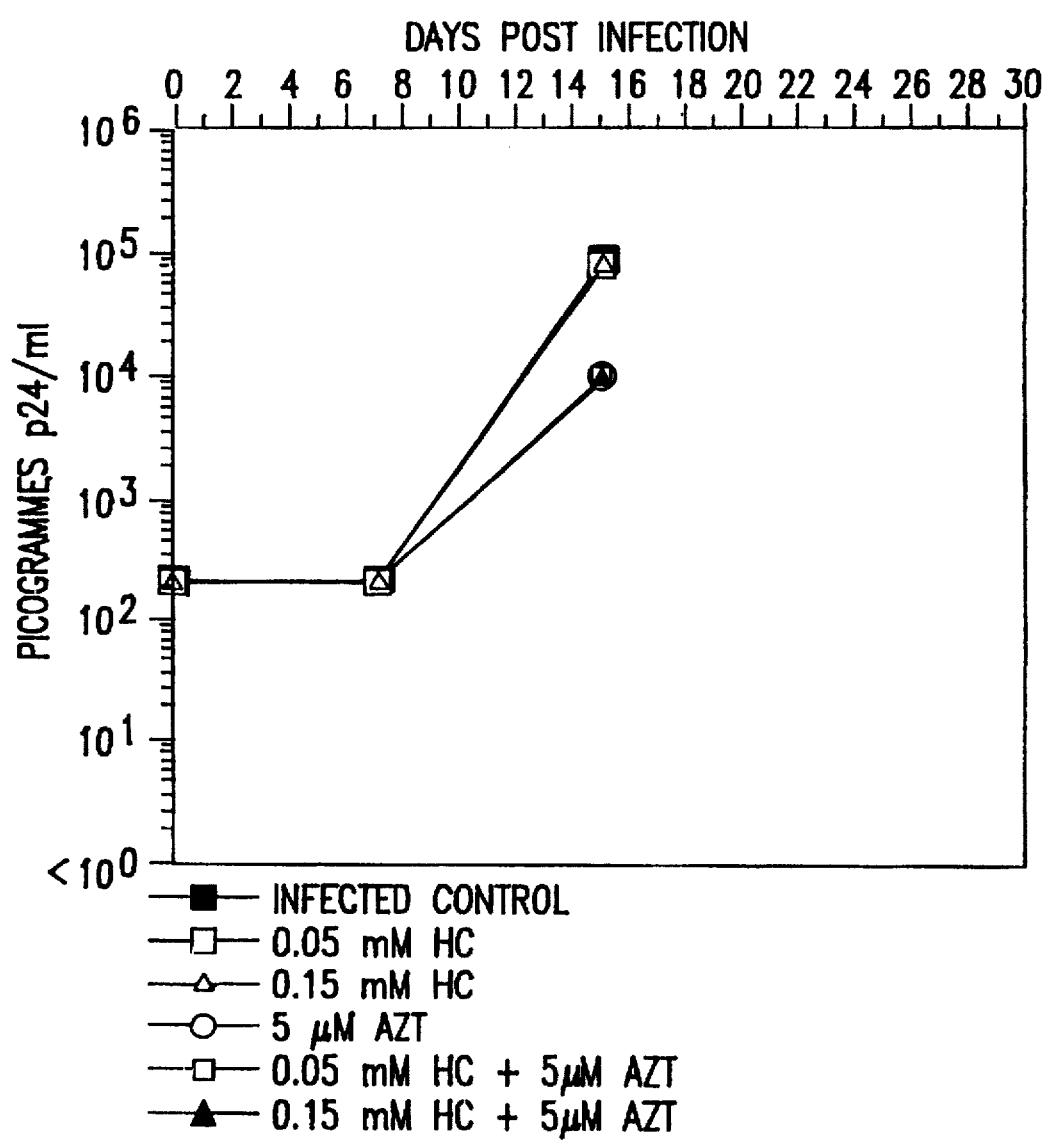
FIG. 2 is a study of the antiviral activity of a mixture of AZT and HC.

As can be seen in FIG. 2, AZT alone at 5 µm has only slight antiviral activity, less than 1 log, (88.4%) inhibition (10030 pg p24/ml compared to 86215 pg p24/ml for infected control), less than ddI at the same dose under the same conditions: 99.1% inhibition (766 pg p24/ml compared to 86215 pg p24/ml for infected control, see FIG. 1). The drug concentrations used here are easily attainable in plasma (plasma concentration achievable under treatment conditions: 4 μM for AZT and 10 μM for ddI (Yarchoan et al, *New Engl. J. Med.* 321 726-738,(1989)).

Comparable proliferative cellular response was observed after stimulation by PHA-IL-2 in all groups. This proliferative response is associated with cytopathic effect in the infected control group, and in the groups treated with HC alone at doses of 0.05 and 0.15 mM and combined with AZT at 5 μM (these groups had greater than 50% loss of viability compared to the uninfected control group). The combination of HC at 0.05 mM and at 0.15 mM with AZT at 5 μM (10108 and 9166 pg p24/ml, respectively) does not modify the viral replication profile compared to AZT alone (FIG. 2).

The results show that the synergistic effect which eradicates HIV replication in $CD4^+$ cells non-activated by PHA-IL-2 (Example 1) is not found from the mixture of HC with AZT.

In FIG. 2, there is shown a study of the activity of the combination of AZT and HC on non-activated $CD4^+$ lymphocytes infected with the HIV virus. The $CD4^+$ lymphocytes were purified from PBMC with immunomagnetic beads (Dynabeads® M450). These cells were infected with the HIV-1 virus strain IIIB at a multiplicity of infection of 5 000 tissue culture infectious dose (TCID) per $10^6$ cells (241 pg/ml p24 antigen equivalent of virus). After 2 hours of virus-cell contact, the cells were washed twice and placed in the culture medium RPMI 1640 (supplemented with 10% FCS, 2 mM glutamine, penicillin 100 IU/ml and streptomycin 100 μg/ml) at a density of $1.3 \times 10^6$ cells/ml. AZT was immediately added at a concentration of 5 μM and HC at a concentration of 0.05 mM and 0.15 mM. The drugs and culture medium were partially renewed (50%) on day 4, maintaining the same concentration of each. On day 7, in order to remove the drugs, the cells were washed twice and put back in culture in the presence of PHA at a concentration of 1 μg/ml and recombinant IL-2 at a concentration of 20 U/ml. This culture was maintained until day 25, with partial renewal (50%) of the medium twice a week. The number of viable cells was quantified by a tetrazolium-based colorimetric 3-(4,5-dimethylthiazol-2-yl)-2,5-diphenyltetrazolium bromide (MTT) method (Pauwels, R. et al *J. Virol. Methds*, 20,309-321, (1988)), and activity is expressed as a percentage of the signal in the drug-free and virus-free control. Viral replication was quantified by measuring the HIV-1 p24 antigen by ELISA using the Dupont de Nemours kit.

EXAMPLE 3

A further study demonstrated inhibition or viral spread in preactivated PBMC culture infected with the HIV virus, by the mixture of HC and ddI. PBMC preactivated with PHA and IL-2, were infected and treated by HC at 0.15 mM; this concentration corresponds to the $IC_{50}$ (inhibitory concentration 50%) after 3 days measured by MTT test, with cellular viability>90% (this cell viability was determined by treating the cells with 2 % Trypan Blue for 2 min and monitoring for dye exclusion). The combination of 0.15 mM of HC and 10 μM of ddI does not modify the $IC_{50}$ and cellular viability.

As can be seen (FIG. 3), the virus replicated rapidly in the non-treated culture maintaining a stable level as from day 6 (day 6=71815; day 12=72750; day 20=62750 pg p24/ml). Treatment with ddI alone at 10 μM and HC alone at 0.15 mM induces inhibition of 97.1% (2071 pg p24/ml) and 82.6% (12500 pg p24/ml) respectively at day 6. By contrast, a major synergistic effect is observed with the combination of 10 μM ddI and 0.15 mM HC, with an inhibition of 99.8% (100 pg p24/ml) at day 6 and no residual viral production datectable (<1 pg. p24/ml) at day 12 and day 20.

This major synergistic effect, having been demonstrated with non-activated lymphocytes, where the combination of ddI with HC eradicates the HIV infection from the cells, is also observed here where lymphocytes are preactivated and treated with the combination of ddI and HC while the PBMC are replicating.

Figure 3:
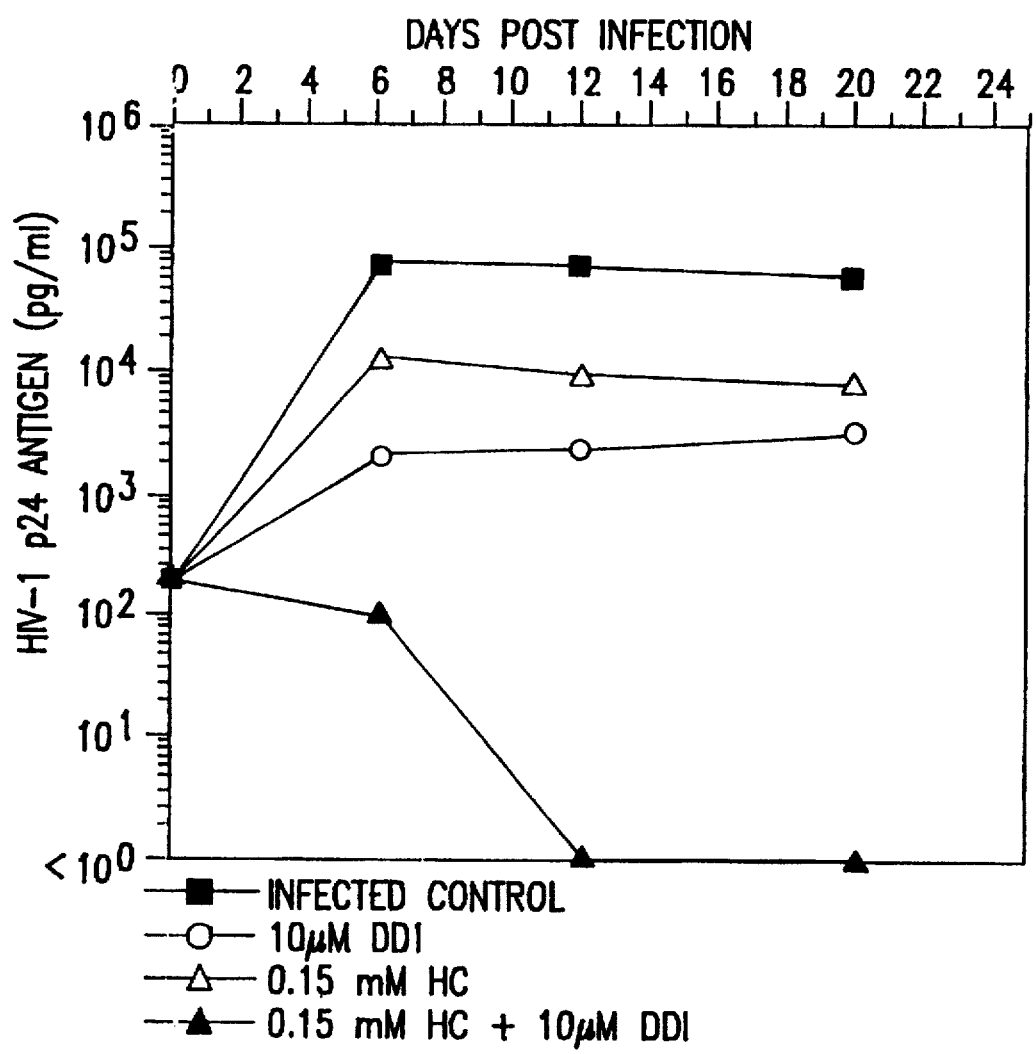
FIG. 3 illustrates the inhibition of viral spread by the mixture of HC and ddI in pre-activated peripheral blood mononuclear cells (PBMC) culture infected with the HIV virus.

In FIG. 3, there is shown the elimination of viral replication by the combination of HC and ddI in preactivated PBMC culture infected with the HIV virus. The PBMC were purified from peripheral blood by discontinuous Ficoll density gradient centrifugation. The cells were grown at a density of $1.3 \times 10^6$ cells/ml in RPMI 1640 medium supplemented with 10% FCS, 2 mM glutamine, penicillin 100 IU/ml and streptomycin 100 μg/ml, in the presence of PHA at a concentration of 1 μg/ml and recombinant IL-2 at 20 U/ml for 72 hours, then infected by HIV-1 strain IIIB at a multiplicity of 5000 TCID for $10^6$ cells (241 pg/ml p24 antigen equivalent of virus). In FIG. 3, the first time point represents viral infection of the cells. After 2 hours of virus-cell contact, the cells were washed twice and placed in the culture medium containing IL-2 but without PHA in the presence of ddI at a concentration of 10 μM and of HC at a concentration of 0.15 mM. These cultures were maintained for 20 days, with partial renewal of the medium and of the two drugs twice a week maintaining the initial concentration. At day 6 and day 14 fresh uninfected donor PBMC were added ($5 \times 10^5$/ml) to replenish aged cultures (*Nature*, 361:1993, 650-654). The number of viable cells was quantified by a tetrazolium-based colorimetric 3-(4,5-dimethylthiazol-2-yl)-2,5-diphenyltetrazolium bromide (MTT) method (Pauwels, R. et al *J. Virol. Methods*, 20:309-321, (1988)), and activity is expressed as a percentage of the signal in the drug-free and virus-free control. Viral replication was quantified by measuring the HIV-1 p24 antigen by ELISA using the Dupont de Nemours kit.

Gao et al in *Proc. Nat'l. Acad. Sci. USA*, cited supra, teach that "human immunodeficiency virus type 1 (HIV-1) viral DNA synthesis in quiescent and activated peripheral blood lymphocytes (PBLs) was studied. Incomplete viral DNA (previously demonstrated to be associated with HIV-1 virions) is carried by HIV-1 virions into quiescent and activated PBLs, contributing to the formation of an early viral DNA pool in these cells. The viral DNA is subsequently completed but only extremely slowly and inefficiently in quiescent PBLs compared to that in stimulated PBLs. We find that this correlates with significantly lower levels of dNTP substrates in quiescent compared to activated PBLs. At these low dNTP concentrations, HIV-1 reverse transcriptase acts in a partially distributive manner. Increasing dNTP concentrations from the levels of quiescent PBLs to the levels of activated PBLs increases the processive action of the reverse transcriptase, which in turn stimulates rapid and efficient formation of full length DNA. Furthermore, hydroxyurea treatment of stimulated PBLs decreases the dNTP levels and the DNA synthesis rate to levels comparable to quiescent PBLs. Our data therefore indicate that low levels of dNTP may explain why HIV-1 DNA is synthesized slowly and inefficiently in quiescent PBLs and suggest that pharmacologic induction of low dNTP levels represents a therapeutic approach for inhibition of HIV-1 replication."

The explanation by Gao et al given for slow and inefficient HIV-1 viral DNA synthesis in quiescent PBLs may well be valid, given that viral DNA is synthesized completely in PBLs under conditions of sufficient replication/activation (Fauci, 1993, *Science*, 262:1011-1018.).

However, Gao et al fail to explain how HC (hydroxycarbamide or hydroxyurea) by means of its inhibitory action on ribonucleotide reductase, and the reduction of dNTP pools in activated lymphocytes, would constitute a potential use of HC in the treatment of patients with AIDS. At the concentration of 1 mM, HC partially reduces the various dNTP pools studied, see FIG. 4(a).

A comparison of table 1 (dNTP pools in quiescent and PHA stimulated PBLs) of Gao et al, and FIG. 4(a) (effect of AC on dNTP pools in PHA-stimulated PBLs) shows that the reduction of pool levels in table 1 is substantially greater than the HC-induced reduction over an equivalent 48 hour period. (See table 1).

If one accepts what Gao et al hypothesize that viral DNA synthesis in "resting" cells while slow and inefficient eventually produces complete viral DNA capable of integration, it is difficult to understand how, under the conditions described, HC could have activity in AIDS patients. It is demonstrated in the present disclosure (FIG. 1) that quiescent cells in the presence of HC at nontoxic concentrations are incapable of preventing the production of infectious virions as measured by the HIV 1 p24 antigen in the supernatant after stimulation by PHA and IL-2.

An explanation of the HC-induced depletion of the dNTP pools which "significantly reduces the rate of HIV-1 DNA synthesis and inhibits the completion of viral DNA synthesis in PHA stimulated PBLs", see FIG. 4(b) of Gao et al, would be that HC at the concentration of 1 mM is cytotoxic for non-activated lymphocytes pretreated for 24 hours and activated by PHA and IL-2 for the following 48 hours in the presence of HC. Under such conditions, greater than 70% of the PBLs die due to the drug's toxicity.

Under the heading "Potential use of hydroxyurea in AIDS therapy", Gao et al state that "by depleting the cellular dNTP pool, hydroxyurea in expected to increase the therapeutic effect of nucleoside analogs 3'-azido 3'-deoxythymidine, dideoxyinosine, or dideoxycytosine, which act as competitors of cellular dNTP". If this were true, one would expect that, in the treatment of infected "resting" cells where dNTP pools are found at their lowest levels, nucleoside analogs would have a major effect, However, as shown in the present disclosure, (FIGS. 1 and 2) the treatment of "resting" cells infected by HIV-1 for seven days and treated by AZT alone at 5 µM has only a slight effect on viral replication as measured by p24 antigen Similarly, for ddI alone, at the same concentration, and under the same conditions, viral replication is only temporarily and partially inhibited, regaining the level of the infected control at day 25 (FIG. 1). It is not, therefore, in accepting the Gao et al explanation that one could have predicted an increase in the therapeutic effect in AIDS therapy by associating a nucleoside analog with HC, all the more so since the results in the present disclosure show that a surprising synergistic effect is observed for the association of HC and ddI, but not at all for HC and AZT.

The subject of the present invention is also a new composition for the treatment of a cell population in the presence of a retrovirus. Additionally, the invention includes a pharmaceutical composition intended, in particular, for the treatment and prevention of retroviral infections, especially those linked to HIV and AIDS wherein the composition contains a synergistic combination of hydroxycarbamide (HC) and a reverse transcriptase inhibitor, in particular a synergistic combination of a dideoxy-nucleoside except AZT and hydroxycarbamide, most preferably a synergistic combination of dideoxyinosine and hydroxycarbamide as active principle, in a pharmaceutically acceptable vehicle. The composition of the invention can also contain inert or pharmacodynamically active additives, carriers and/or excipients.

The pharmaceutical composition of the invention can take the form of a lyophilized powder of the active substance, to be dissolved immediately before use in a physiological solution for the purpose of injection. The medicament can then be administered parenterally, for example intravenously, intraperitoneally, in the cerebrospinal fluid, and the like. For injection, the active principle is dissolved in a physiological solution until the desired concentration for administration is obtained.

The pharmaceutical composition according to the invention can also take a form which is suitable for oral administration. For example, suitable forms are tablets, hard gelatin capsules, dragées, powders and granules. The formation of such oral forms is well-known to those skilled in the art. Any of the known formulations are useful in preparing the instant oral pharmaceutical compositions.

As regards the dosage of the medicament according to the invention, it will be clear to the artisan that the doses to be administered are variable according to the treatment period, and frequency of administration, the host, and the nature and severity of the disease and that the dosages can be easily determined without any undue mount of experimentation.

The compositions of the invention are administered in substantially non-toxic dosage concentrations sufficient to insure the release of a sufficient dosage unit of the present synergistic combination into the patient to provide the desired inhibition of the spread of the retrovirus. The actual dosage administered will be determined by physical and physiological factors such as age, body weight, severity of condition, and/or clinical history of the patient. With these considerations in mind, the dosage of the instant synergistic combination for a particular subject can be readily determined by the physician. It might be noted that in extreme cases a dosage approaching the toxic level may be the acceptable treatment protocol.

For example, in the treatment of HIV-infected and AIDS patients, the composition can comprise from about 1 to 66 mg/Kg/day of ddI and from about greater than 5 mg/Kg/day to about 20 mg/Kg/day of HC.

The invention also covers the use of hydroxycarbamide (HC) and dideoxyinosine in combination with other medicinal compositions intended for the treatment of retroviral infections and tumors. Immunostimulants and immunomodulators such as for example cytokines, including IL-2, IL-12 and interferon molecules can be used in combination with the present invention.

A preferred range for in vitro administration of the compositions of the present invention includes hydroxycarbamide in a concentration greater than 0.05 mM and less than or equal to 0.15 mM in combination with a dideoxynucleoside except AZT such as ddI at concentrations which are generally known and used in the art. A preferred embodiment of the present invention utilizes HC at 0.15 mM and the dideoxynucleoside such as ddI in a range of between about 0.01 µM to about 100 µM, preferably between about 2.5 µM to about 25 µM, most preferably from about 5 µM to about 10 µM.

Anti-HIV Activity of the Combination of Didanosine and Hydroxyurea in HIV-1 Infected Individuals HIV is known to be present in massive amounts in both resting and actively replicating cells in infected individuals.

The combination of ddI and hydroxyurea was tested in a number of asymptomatic patients. After three months of treatment, which was well tolerated, a reduction was observed of viral load in all patients, down to non-quantifiable levels in half our population, accompanied by an average rise in CD4 count from below normal to within normal range. These results are described hereinbelow.

Resting lymphocytes are an important reservoir of virus in infected individuals, and a high HIV burden has also been observed in lymphoid tissue as intercellular virus in latent form (Embretson J., Zupancic M., Ribas J. L., et al. Massive covert infection of helper T lymphocytes and macrophages by HIV during the incubation period of AIDS. *Nature*, 1993; 362: 359–362). Recently published data on the dynamics of cellular turnover and viral replication suggest that from early stages of infection there is massive viral production by actively replicating lymphocytes (Wei X., Ghosh S., Taylor M., et al. Viral dynamics in human immunodeficiency virus type 1 infection, *Nature*. 1995; 373: 117–122). It is therefore important that antiretroviral chemotherapy be capable of suppressing HIV in resting and in activated cells (Malley S., Grange J., Hamedi-Sangsari F., Vila J. Suppression of HIV production in resting lymphocytes by combining Didanosine and hydroxamate compounds. Lancet 1994; 343: 1292).

EXAMPLE 4

The tolerance and the antiviral activity of the combination of hydroxyurea (HU) and ddI was tested in a number of asymptomatic volunteer subjects considered to be relatively immunocompetent based on their asymptomatic status and CD4 count.

The study of HU and ddI in this trial was approved by the ethics committee of the University of Saint Etienne, France. All patients gave their informed consent. Twelve HIV-1 seropositive subjects, nine male and three female, age range 26 to 60, with CD4 counts between 263 and 582, asymptomatic previously untreated, and with a hematological profile corresponding to grade 0 of the WHO classification, were included. They were treated for 90 days with 200 mg ddI twice daily, and 500 mg HU twice daily taken at least one hour after the ddI.

The first objective was to evaluate the side effects of this drug combination. Patients were monitored every two weeks for clinical and hematological status, and for biological parameters associated with renal, hepatic and pancreatic function.

The second objective was to evaluate immune status and viral load. CD4, CD8 and β2-microglobulin were quantified at days 0 and 90. p24 Ag, quantitative plasma and cell viraemia and RNA PCR were evaluated at days 0 and 90. For those patients for whom no virus was detectable by these methods, recovery of the virus from activated PBMC was attempted.

Particle-associated RNA in plasma was quantified with a PCR-RNA system: the PCR Amplicor HIV Monitor (Roche Diagnostic Systems (Sninsky J., Kwok S. The application of quantitative polymerase chain reaction to therapeutic monitoring. *AIDS* 1993; 7 (suppl 2): S29–S34). This ultra sensitive assay has a defection limit of approximately 200 copies of RNA per milliliter of plasma. In those cases where viral RNA was below the detection limit, we adopted a qualitative technique by increasing the number of amplification cycles to 40. Infectious HIV in PRMC and plasma was quantified as described in (Rouzioux C., Puel J., Agut H. et al. Comparative assessment of quantitative HIV viraemia assays. *AIDS*. 1992; 6: 373–377). When infectious virus was undetectable by this technique, the PBMC was activated with 1 µg/ml PHA and 20 units/ml II-2 which we cultivated alone, and with PBMC from healthy donors. On days 7, 14 and 21 we tested for HIV-1 p24 gag Ag (Elisa assay, Dupont).

RESULTS

Overall tolerance was good. No patient interrupted treatment due to clinical or biological side-effects. Patient No. 10 complained of minor digestive disorders during the first ten days of treatment. One female patient No. 11 exhibited hyperpigmentation of the palms, another No. 6 complained of paresthesis of the right arm from days 45 to 90. Clinical examination of the latter was normal on these days and her electromyogram was normal on day 90. Patient No. 1 experienced minor ulcerations of the mouth lasting from days 60 to 90. An increase in mean corpuscular volume was observed in all patients with an average volume at day 90 of 102.2 fl. No changes in RBC, WBC, platelets, hemoglobin, amylases, lipases or transaminases were noted.

As shown in the table, at day 90 eleven of the twelve patients had increased their CD4 count, some by a very substantial amount. Avenge CD4 count in our population was 392 at day 0 (avenge relative percentage 22.6%), and 573 at day 90 (average relative percentage 30.1%), with a mean increase of 181 cells (mean relative percentage increase 7.5%).

Nine of the twelve patients remained within normal β2-microglobulin ranges during treatment. Patient 2 showed a decrease but remained above the norm, patient 1 achieved normal range, and patient 4 remained abnormal.

Using the PCR RNA technique, plasma viral load was quantified in all patients before treatment, with values ranging from 3521 to 128973 copies per ml of plasma. At day 90, six patients showed no detectable viral load using the PCR RNA quantitative method. The viral load of the other six patients remained detectable but showed a substantial decrease of between 95.6% and 99.8%, with a mean decrease of 2.04 log. In order to verify the non-detectability of the viral load in the six patients, the number of amplification cycles was increased as described above. The presence of viral RNA in the plasma of patients 7 and 8 was detected, whereas viral RNA remained negative for patients 9, 10, 11 and 12.

Using the TCID 50 % technique, infectious virions in the plasma of eleven patients at day 0 were not detected. The levels of infectious HIV-1 were also detected and quantified at day 0 in the PBMC. Virus was quantified in eleven patients (ranging from<1 to 234.16 TCID 50% per $10^6$ cells), whereas patient 8 required PBMC activation to reveal the presence of virus. After 90 days of treatment, the virus was unquantifiable in seven subjects. The viral load of the other five patients remained detectable but showed a substantial decrease of between 94.7%; and 98.5%, with a mean decrease of 1.60 log.

The PBMC of the five patients for whom, after 90 days of treatment, no infectious virus (TCID 50% per $10^6$ cells) was quantifiable, and no viral RNA was detectable was activated, using the technique described above. No infectious virus was detected in any of the five patients by this method.

These results indicate that 90 days of treatment with the combination of hydroxyurea and didanosine is well tolerated in this patient population of previously untreated asymptomatic HIV-infected individuals, and induces a marked reduction in viral load for all patients, which in half of the cases studied results in the apparent suppression of HIV in the peripheral blood. The reduction in viral load is accompanied by a substantial avenge increase in CD4 count, achieving a mean count which falls within the normal range. The average CD4 increase of the six subjects for whom no viral RNA was quantifiable at day 90 was 283. Even though this was not a randomized trial, these results exceed those observed historically for zidovudine or didanosine alone.

Preliminary pharmacokinetic data indicate that, following oral administration of 500 mg HU, peak plasma concentration is 0.15 mM per liter. This concentration is roughly equivalent to that reported to result in the suppression of HIV when combined with ddI in vitro.

All of the references cited hereinabove are expressly incorporated herein, in toto, by reference thereto.

The invention has been described with reference to specific and preferred embodiments. It will be recognized by those skilled in the art that numerous changes and substitutions may be made without departing from the spirit and scope of the invention.

7. The method of claim 6, wherein the amount of dideoxynucleoside is such as to provide a concentration of about 5 µM and the amount of hydroxycarbamide is such as to provide a concentration of about 0.15 mM.

8. The method of claim 6, wherein the amount of dideoxynucleoside is such as to provide a concentration of about 10 µM and the amount of hydroxycarbamide is such as to provide a concentration of about 0.15 mM.

9. A composition useful for inhibiting retroviral replication comprising hydroxycarbamide and the dideoxynucleosides 2',3'-dideoxyinosine (ddI) and 2',3'-didehydro-3'-deoxythymidine (d4T).

10. The composition of claim 9, wherein the retrovirus is HIV.

11. The composition of claim 10, wherein the HIV is HIV-1.

12. The composition of claim 9, wherein the amount of dideoxynucleoside is such as to provide a concentration of about 0.01 µM to 100 µM and the amount of hydroxycarbamide is such as to provide a concentration greater than 0.05 mM and equal to or less than about 0.25 mM.

TABLE

Virological and immunological data at baseline and after three months' treatment with a combination of didanosine and hydroxyurea

| Patient | Sex | Age (Yr) | Risk factor | CD4+ Cells/mm³ (%) | | PCR RNA RNA copies/ ml plasma | | *RNA detection | Detection of infectious virus | | | | | |
|---|---|---|---|---|---|---|---|---|---|---|---|---|---|---|
| | | | | | | | | | Plasma (TCID$_{50}$/ml) | | PBMC (TCID$_{50}$/10$^6$ cells) | | †PBMC activation | |
| | | | | Day 0 | Day 90 | Day 0 | Day 90 | Day 90 | Day 0 | Day 90 | Day 0 | Day 90 | Day 0 | Day 90 |
| 1 | M | 35 | H | 470 (16) | 401 (22) | 128973 | 156 | | 0 | 0 | 234.2 | 3.5 | | |
| 2 | M | 34 | H | 365 (13) | 584 (23) | 30273 | 1308 | | 2 | 0 | 61.6 | 1.8 | | |
| 3 | M | 29 | H | 311 (20) | 373 (36) | 45580 | 559 | | 0 | 0 | 42.5 | <1 | | |
| 4 | M | 27 | H | 319 (14) | 412 (16) | 12773 | 404 | | 0 | 0 | 19.0 | <1 | | |
| 5 | M | 60 | BS | 321 (36) | 364 (32) | 115356 | 882 | | 0 | 0 | 3.3 | 0 | | (−) |
| 6 | F | 29 | IDU | 427 (32) | 557 (37) | 43129 | 1591 | | 0 | 0 | 1 | 0 | | |
| 7 | F | 28 | He | 318 (25) | 575 (36) | 4375 | non det | (+) | 0 | 0 | 55.9 | <1 | | |
| 8 | M | 43 | AOC | 582 (22) | 813 (35) | 9973 | non det | (+) | 0 | 0 | 0 | 0 | (+) | (−) |
| 9 | M | 26 | H | 560 (28) | 1030 (34) | 11091 | non det | (−) | 0 | 0 | <1 | 0 | | (−) |
| 10 | M | 52 | IDU | 295 (27) | 872 (41) | 3521 | non det | (−) | 0 | 0 | <1 | 0 | | (−) |
| 11 | F | 34 | IDU | 263 (14) | 374 (22) | 12713 | non det | (−) | 0 | 0 | 7.2 | 0 | | (−) |
| 12 | M | 31 | H | 474 (24) | 526 (27) | 13324 | non det | (−) | 0 | 0 | <1 | 0 | | (−) |

H: homosexual. He: heterosexual. BS: bi-sexual. IDU: Intravenous Drug User. AOC: accidental occupational contamination. non det: non detectable (sensitivity threshold = 200 RNA copies/ml). (%): CD4+ cells as a percentage of total lymphocytes. *The symbols in brackets indicate the detection (+) or the absence of detection (−) of viral RNA after 40 amplification cycles. †: The symbols in brackets indicate the detection (+) or the absence of detection (−) of infectious virus after in vitro PBMC activation.

We claim:

1. A method of inhibiting retroviral replication in cells comprising administration to a host in need thereof a combination of hydroxycarbamide and the dideoxynucleosides 2',3'-dideoxyinosine (ddI) and 2',3'-didehydro-3'-deoxythymidine (d4T).

2. The method of claim 1, wherein the retrovirus is HIV.

3. The method of claim 2, wherein the HIV is HIV-1.

4. The method of claim 1, wherein the amount of dideoxynucleoside is such as to provide a concentration of about 0.01 µM to 100 µM and the amount of hydroxycarbamide is such as to provide a concentration greater than 0.05 mM and equal to or less than about 0.25 mM.

5. The method of claim 4, wherein the amount of dideoxynucleoside is such as to provide a concentration of about 2.5 µM to 25 µM and the amount of hydroxycarbamide is such as to provide a concentration greater that 0.05 mM and equal to or less than about 0.25 mM.

6. The method of claim 5, wherein the amount of dideoxynucleoside is such as to provide a concentration of about 5 µM to 10 µM and the amount of hydroxycarbamide is such as to provide a concentration of greater than 0.05 mM and equal to or less than about 0.25 mM.

13. The composition of claim 12, wherein the amount of dideoxynucleoside is such as to provide a concentration of about 2.5 µM to 25 µM and the amount of hydroxycarbamide is such as to provide a concentration greater than 0.05 mM and equal to or less than about 0.25 mM.

14. The composition of claim 13, wherein the amount of dideoxynucleoside is such as to provide a concentration of about 5 µM to 10 µM and the amount of hydroxycarbamide is such as to provide a concentration of greater than 0.05 mM and equal to or less than about 0.25 mM.

15. The composition of claim 14, wherein the amount of dideoxynucleoside is such as to provide a concentration of about 5 µM and the amount of hydroxycarbamide is such as to provide a concentration of about 0.15 mM.

16. The composition of claim 14, wherein the amount of dideoxynucleoside is such as to provide a concentration of about 10 µM and the amount of hydroxycarbamide is such as to provide a concentration of about 0.15 mM.

* * * * *